United States Patent
Brown et al.

(10) Patent No.: US 7,156,854 B2
(45) Date of Patent: Jan. 2, 2007

(54) LENS DELIVERY SYSTEM

(75) Inventors: Kyle Brown, Fort Worth, TX (US); David A. Downer, Fort Worth, TX (US); Thomas M. Heyman, Placentia, CA (US)

(73) Assignee: Alcon, Inc., Hunenberg (CH)

( * ) Notice: Subject to any disclaimer, the term of this patent is extended or adjusted under 35 U.S.C. 154(b) by 623 days.

(21) Appl. No.: 10/446,761

(22) Filed: May 28, 2003

(65) Prior Publication Data

US 2004/0243141 A1    Dec. 2, 2004

(51) Int. Cl.
*A61F 9/00* (2006.01)
(52) U.S. Cl. ...................... 606/107; 623/6.11
(58) Field of Classification Search ............... 606/107, 606/117; 623/6.11, 6.12, 6.18; 604/220, 604/218
See application file for complete search history.

(56) References Cited

U.S. PATENT DOCUMENTS

| | | | |
|---|---|---|---|
| 4,681,102 A | | 7/1987 | Bartell |
| 5,275,604 A | | 1/1994 | Rheinish et al. |
| 5,494,484 A | | 2/1996 | Feingold |
| 5,499,987 A | | 3/1996 | Feingold |
| 5,616,148 A | * | 4/1997 | Eagles et al. ............... 606/107 |
| 5,620,450 A | | 4/1997 | Eagles et al. |
| 5,653,715 A | | 8/1997 | Reich et al. |
| 5,873,879 A | | 2/1999 | Figueroa et al. |
| 5,928,245 A | * | 7/1999 | Wolf et al. .................. 606/107 |
| 5,944,725 A | * | 8/1999 | Cicenas et al. ............. 606/107 |
| 6,241,737 B1 | | 6/2001 | Feingold |
| 6,312,433 B1 | | 11/2001 | Butts et al. |
| 6,355,046 B1 | | 3/2002 | Kikuchi et al. |
| 6,387,101 B1 | | 5/2002 | Butts et al. |
| 6,406,481 B1 | | 6/2002 | Feingold et al. |
| 6,447,519 B1 | | 9/2002 | Brady et al. |
| 6,468,282 B1 | | 10/2002 | Kikuchi et al. |
| 6,471,708 B1 | | 10/2002 | Green |
| 6,491,697 B1 | | 12/2002 | Clark et al. |
| 6,503,275 B1 | | 1/2003 | Cumming |
| 6,506,195 B1 | | 1/2003 | Chambers et al. |
| 7,014,641 B1 | * | 3/2006 | Kobayashi et al. ......... 606/107 |
| 2002/0151904 A1 | | 10/2002 | Feingold et al. |

FOREIGN PATENT DOCUMENTS

EP    1 360 944 A2    11/2003
WO    WO 02/060338    8/2002

* cited by examiner

*Primary Examiner*—(Jackie) Tan-Uyen Ho
*Assistant Examiner*—Natalie Pous
(74) *Attorney, Agent, or Firm*—Jeffrey S. Schira

(57) ABSTRACT

A lens delivery system having a plunger, an injector body and a nozzle portion connected to the injector body, the nozzle portion having a hinged lid and a hollow body with a lens holding platform formed beneath the hinged lid. The cartridge has an elongated nozzle tube or tip with a bore, the bore communicating with the lens holding platform. The bottom of the bore is rounded, which causes the edges of the lens between the lens haptics to fold upwardly as the lens is pushed down the bore from the platform by the plunger. A removable pin fits into the lid and prevents the lens from moving down the bore of the tip during shipment and storage.

18 Claims, 10 Drawing Sheets

LENS DELIVERY SYSTEM

This invention relates to intraocular lenses (IOLs) and more particularly to devices use to inject IOLs into an eye.

BACKGROUND OF THE INVENTION

The human eye in its simplest terms functions to provide vision by transmitting and refracting light through a clear outer portion called the cornea, and further focusing the image by way of the lens onto the retina at the back of the eye. The quality of the focused image depends on many factors including the size, shape and length of the eye, and the shape and transparency of the cornea and lens.

When trauma, age or disease cause the lens to become less transparent, vision deteriorates because of the diminished light which can be transmitted to the retina. This deficiency in the lens of the eye is medically known as a cataract. The treatment for this condition is surgical removal of the lens and implantation of an artificial lens or IOL.

While early IOLs were made from hard plastic, such as polymethylmethacrylate (PMMA), soft, foldable IOLs made from silicone, soft acrylics and hydrogels have become increasingly popular because of the ability to fold or roll these soft lenses and insert them through a smaller incision. Several methods of rolling or folding the lenses are used. One popular method is an injector cartridge that folds the lenses and provides a relatively small diameter lumen through which the lens may be pushed into the eye, usually by a soft tip plunger. The most commonly used injector cartridge design is illustrated in U.S. Pat. No. 4,681,102 (Bartell), and includes a split, longitudinally hinged cartridge. Similar designs are illustrated in U.S. Pat. Nos. 5,494,484 and 5,499,987 (Feingold) and U.S. Pat. Nos. 5,616,148 and 5,620,450 (Eagles, et al.). In an attempt to avoid the claims of U.S. Pat. No. 4,681,102, several solid cartridges have been investigated, see for example U.S. Pat. No. 5,275,604 (Rheinish, et al.) and U.S. Pat. No. 5,653,715 (Reich, et al.).

These devices all require that the lens be shipped separately from the cartridge. This requires that the lens be removed from its shipping container and placed in the cartridge prior to use. This requires additional handling of the lens, with the resulting potential for damage to the lens. One prior art device, disclosed in U.S. Pat. No. 6,471,708 B1 (Green), the entire contents of which being incorporated herein by reference, discloses a lens delivery system that is also suitable for use as a lens shipment container. As shown in FIGS. 6A–6C of this patent, the disclosed device does not fold the lens, but rather compresses or crushes the lens. Such a device works with robust, rubbery, elastic lens materials, but such a design is less than optimal when used with a viscoelastic material, such as a soft acrylic. Accordingly, a need continues to exist for a lens delivery system suitable for use with a lens made from a viscoelastic material and in which the lens can be shipped.

BRIEF SUMMARY OF THE INVENTION

The present invention improves upon prior art by providing a lens delivery system having a plunger, an injector body and a nozzle portion connected to the injector body, the nozzle portion having a hinged lid and a hollow body with a lens holding platform formed beneath the hinged lid. The inside of the hinged lid contains ribs that help to hold a lens stationary on the platform when the lid is closed. The cartridge has an elongated nozzle tube or tip with a bore, the bore communicating with the lens holding platform. The bottom of the bore is rounded, which causes the edges of the lens between the lens haptics to fold upwardly as the lens is pushed down the bore from the platform by the plunger. The central portion of the optic of the lens is prevented from moving upward during folding by a projection in the lid between the ribs. A removable pin fits into the lid and prevents the lens from moving down the bore of the tip during shipment and storage. The plunger and injector body contain a ratcheting mechanism that helps prevent the plunger from moving during shipment and storage. The system of the present invention allows the lens to be stored, shipped and delivered into an eye without any additional devices and without handling the lens. The folding mechanism of the present invention is also suitable for folding lenses made from a soft acrylic material as well as other materials such as silicones and hydrogels.

It is accordingly an object of the present invention to provide a lens delivery system suitable for the storage, shipment and delivery of a lens into an eye without the use of any additional devices.

It is a further object of the present invention to provide a lens delivery system that is suitable for folding lenses made from a soft acrylic material.

It is a further object of the present invention to provide a lens delivery system having a removable pin that limits movement of the lens in place during storage and shipment.

Other objects, features and advantages of the present invention will become apparent with reference to the drawings, and the following description of the drawings and claims.

DETAILED DESCRIPTION OF THE INVENTION

Figure 1:
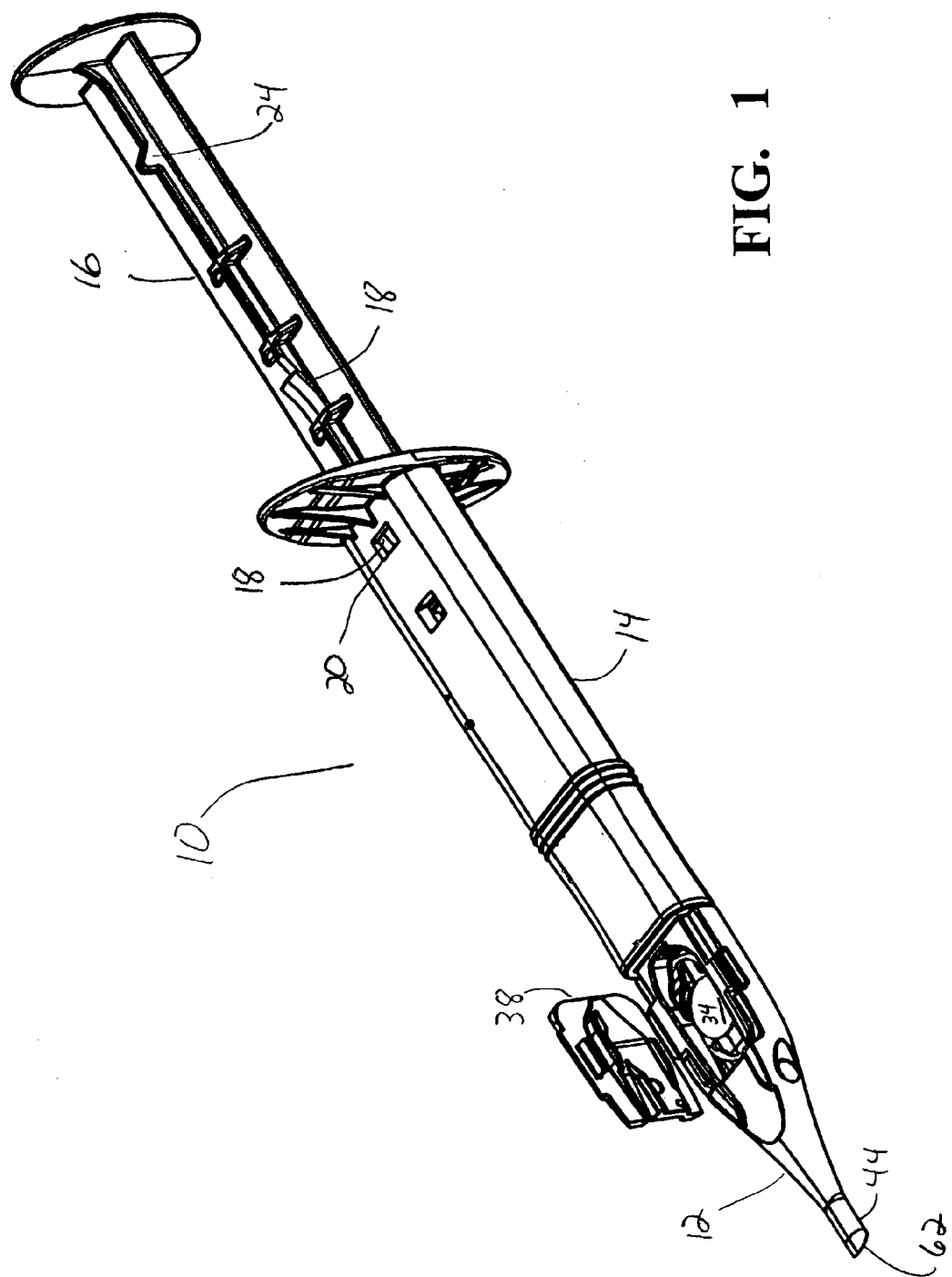
FIG. 1 is a perspective view of the lens delivery system of the present invention.
Figure 10:
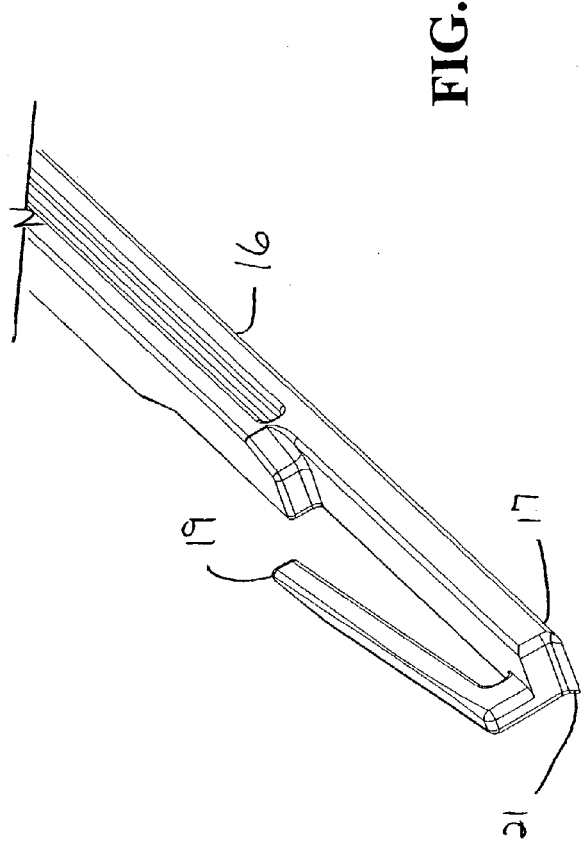
FIG. 10 is a partial perspective view of the plunger tip that may be used with the present invention.
Figure 11:
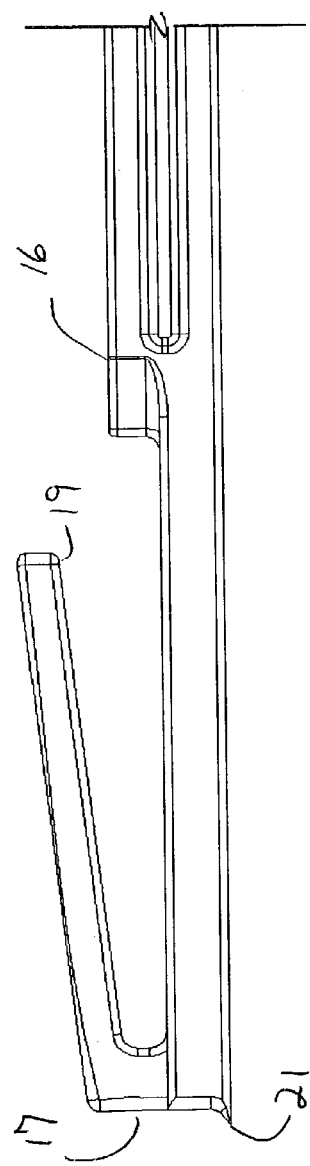
FIG. 11 is a side elevational view of the plunger tip that may be used with the present invention.

As best seen in FIG. 1, lens delivery system 10 of the present invention generally includes nozzle portion 12, injector body 14 and plunger 16. Plunger 16 contains a plurality of spring tabs 18 that cooperate with slot 20 on injector body 14 to prevent unwanted or unintended rearward (proximal) movement of plunger 16 during shipment or use. Plunger 16 also contains rigid tab 24 that cooperates with injector body 14 to prevent plunger 16 from being pushed too far forward (distally) during use. Nozzle portion 12, injector body 14 and plunger 16 are preferably molded from a suitable thermoplastic, such as polypropylene. As best seen in FIGS. 10 and 11, distal tip 17 of plunger 16 contains biasing tab 19 that holds tip 17 tightly within injector body 14 during shipment, but allows tip 17 to pass through relatively small distal nozzle tube 44 during delivery of IOL 34. Chin 21 on tip 17 helps keep tip 17 from being pushed up and over IOL 34 during delivery of IOL 34.

Figure 2:
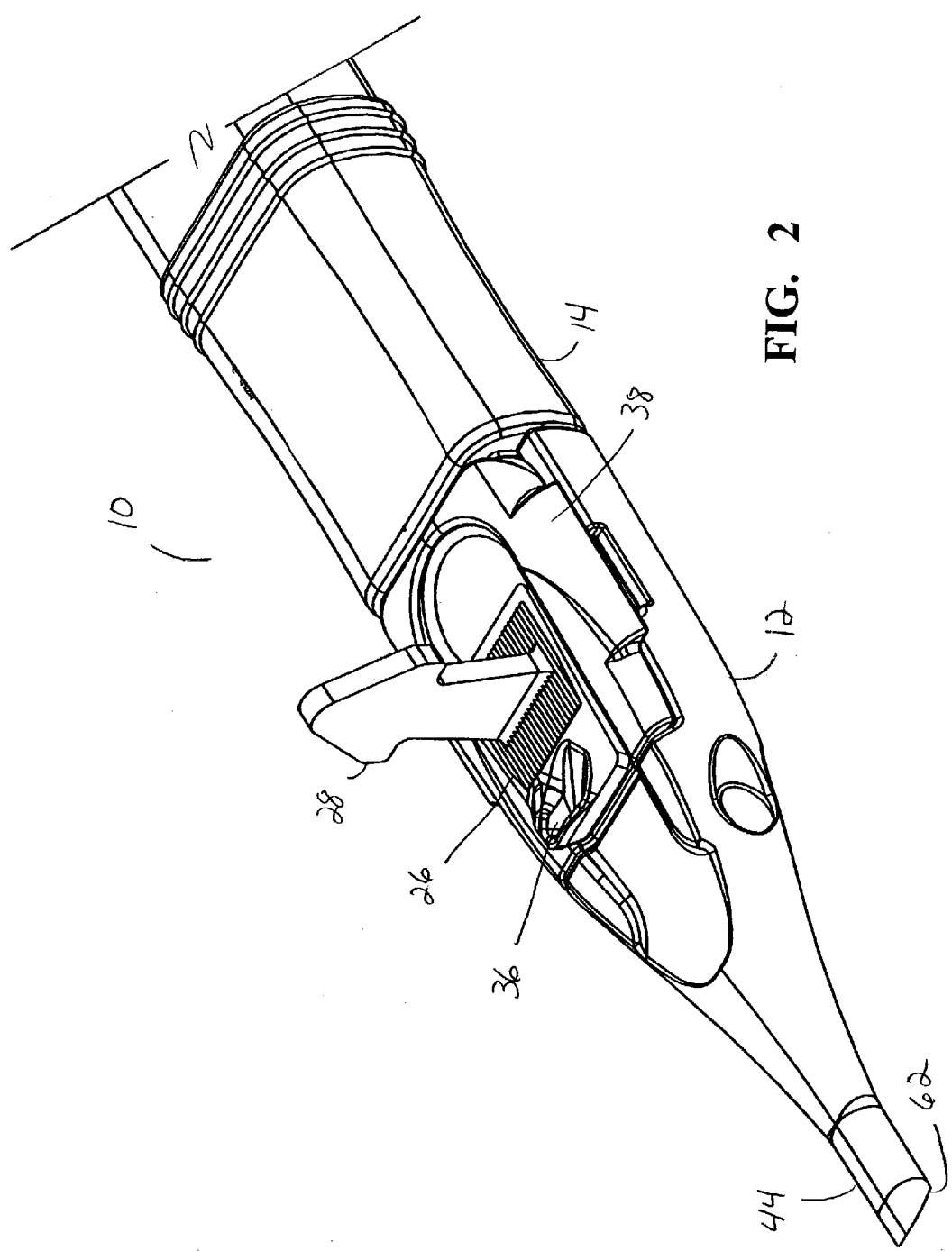
FIG. 2 is an exploded perspective view of the cartridge used with the lens delivery system of the present invention, showing the cartridge with the lens stop in place.
Figure 3:
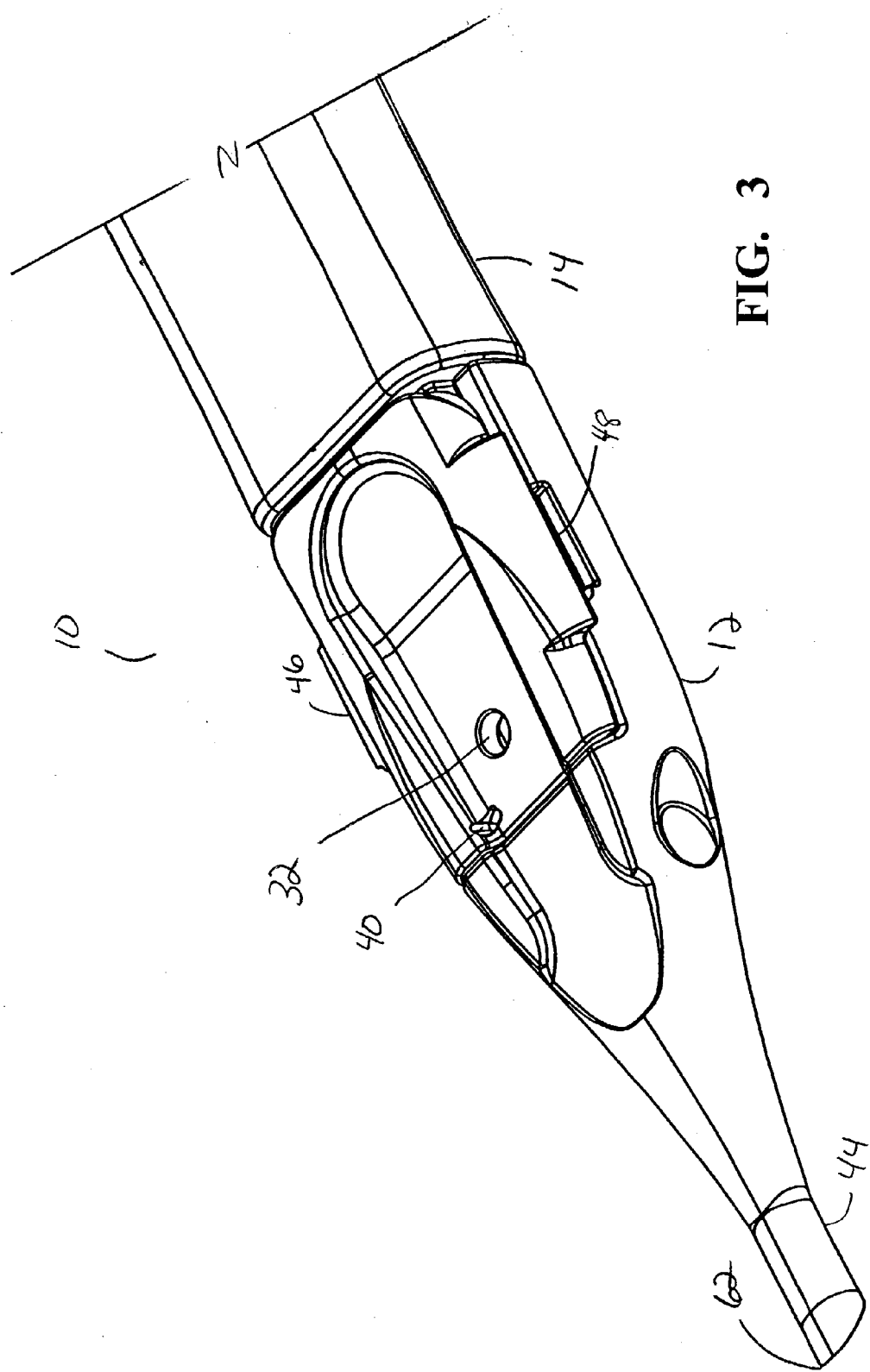
FIG. 3 is an exploded perspective view of the cartridge used with the lens delivery system of the present invention, showing the cartridge with the lens stop removed.
Figure 4:
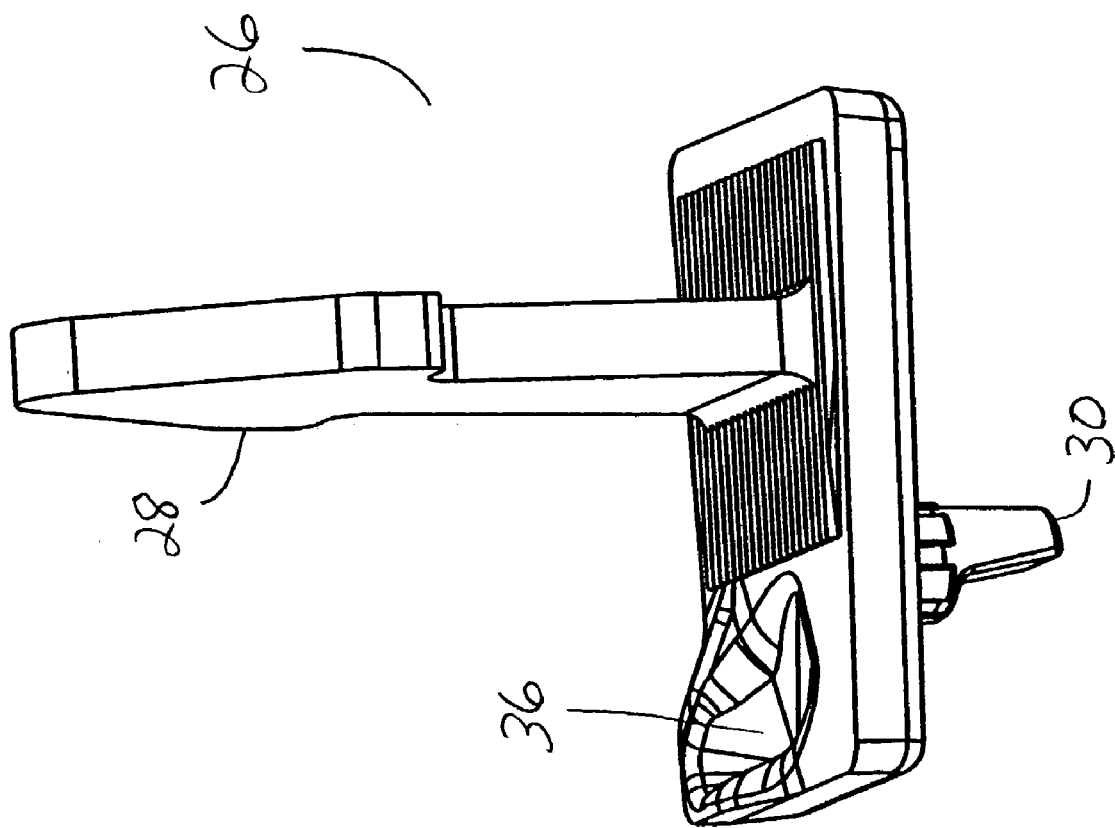
FIG. 4 is an exploded perspective view of the lens stop used with the lens delivery system of the present invention.

As best seen in FIGS. 2, 3 and 4, system 10 of the present invention may include removable stop 26 that frictionally engages nozzle portion 12. Stop 26 contains finger tab 28 to facilitate removal of stop 26 from nozzle portion 12. Stop 26 contains pin 30 that fits into hole 32 in lid 38 of nozzle portion 12 when stop 26 is mounted on nozzle portion 12. Pin 30 limits the forward movement of the distal edge of optic 34 of IOL 35 when IOL 35 is contained within nozzle portion 12 during shipment. Preferably, pin 30 contains a feature, such as a lip or a ridge formed upon assembly by deformation of pin 30 to help lock pin 30 within hole 32. Stop 26 and pin 30 help to prevent distal movement of IOL 34 during shipment. Stop 26 may also contain channeled port 36 that is fluidly connected to port 40 in lid 38 of nozzle portion 12. Channeled port 36 in combination with port 40 allows a suitable viscoelastic material (VISCOAT®, PROVISC®) to be injected into nozzle portion 12 without raising lid 38. The viscoelastic material assists in the expression of lens 34 out of nozzle portion 12. The location of channeled port 36 and port 40 assure that when the viscoelastic material is injected into nozzle portion 12, the viscous nature of the material pushes leading haptic 42 proximally toward lens 34, thereby assisting in folding lens 34. Channeling of channeled port 36 assists in locating port 36 with the relatively small cannula used to inject the viscoelastic material. Stop 26 preferably is molded from a plastic suitable for injection molding.

Figure 5:
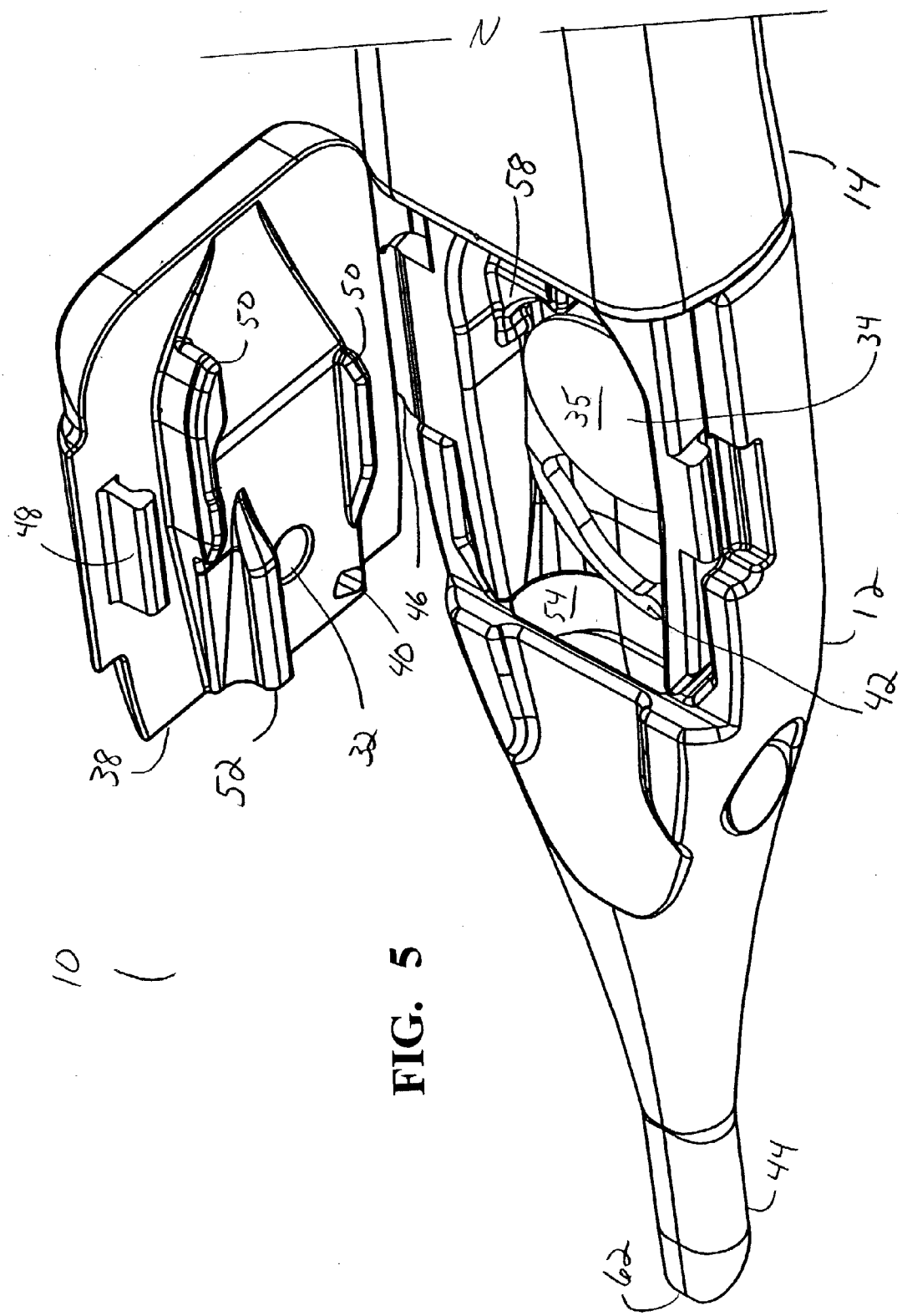
FIGS. 5–7 are exploded perspective views of the cartridge used with the lens delivery system of the present invention, showing the cartridge with the lens stop removed and the hinged lid open to expose the lens.
Figure 6:
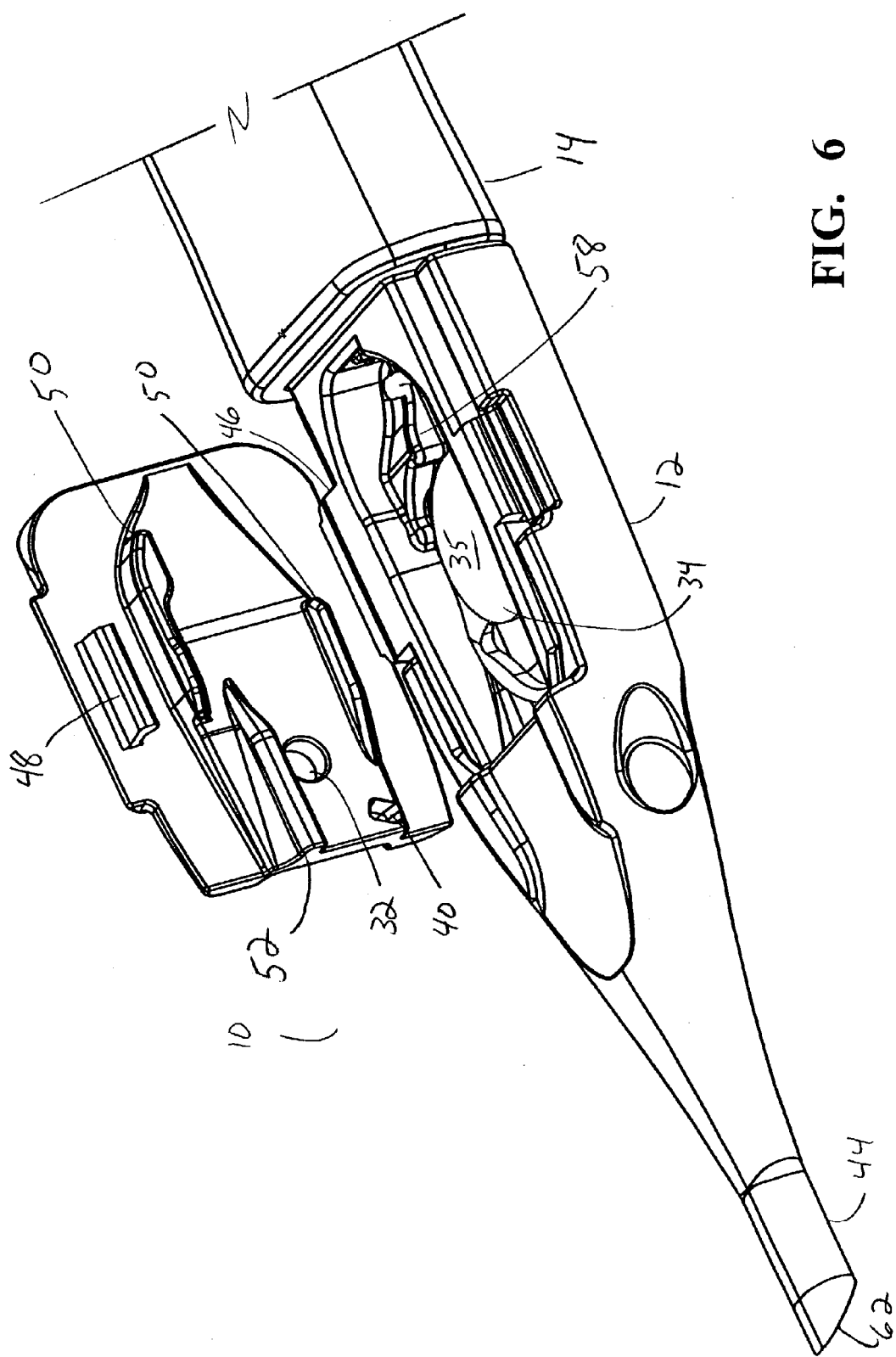
Figure 7:
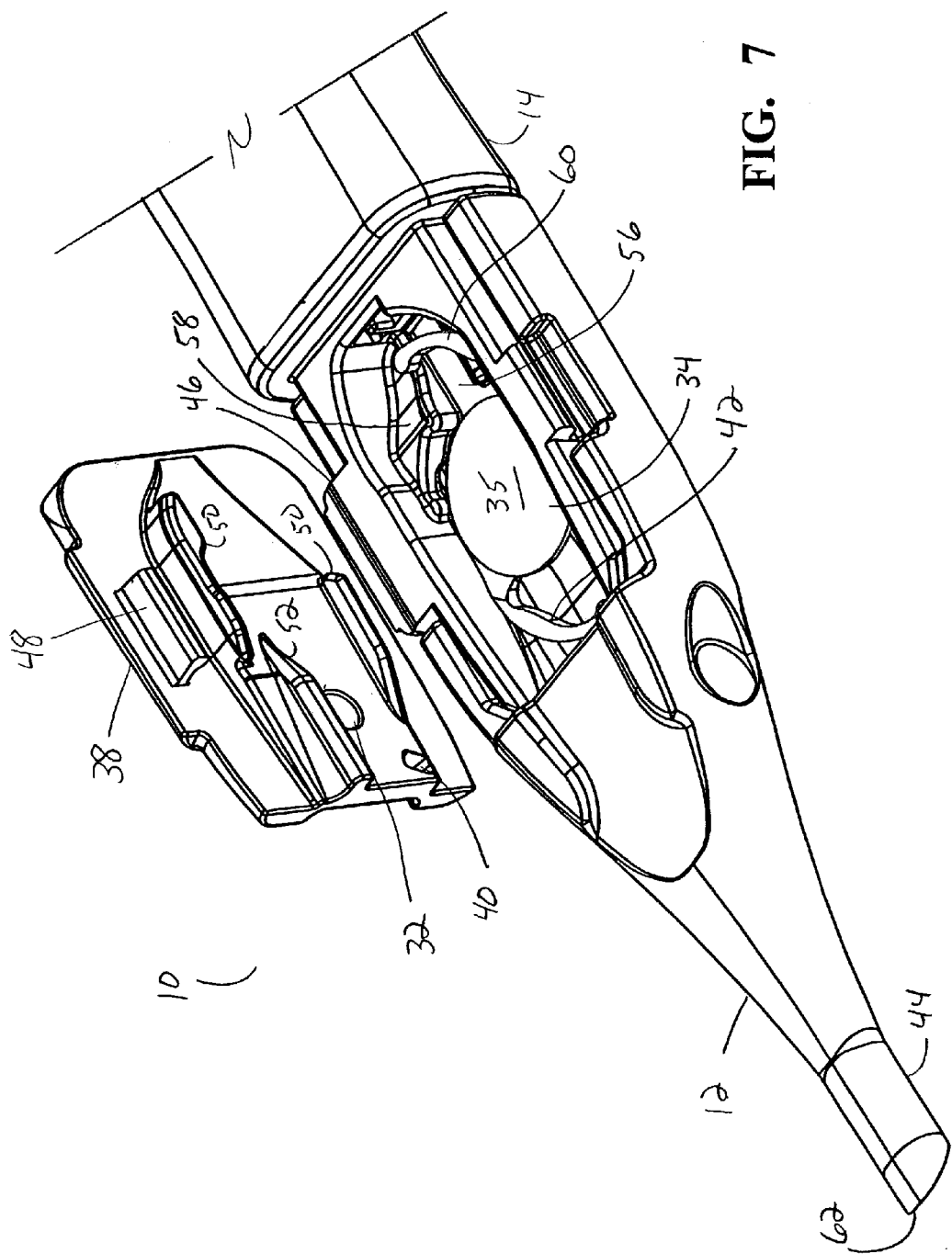
Figure 8:
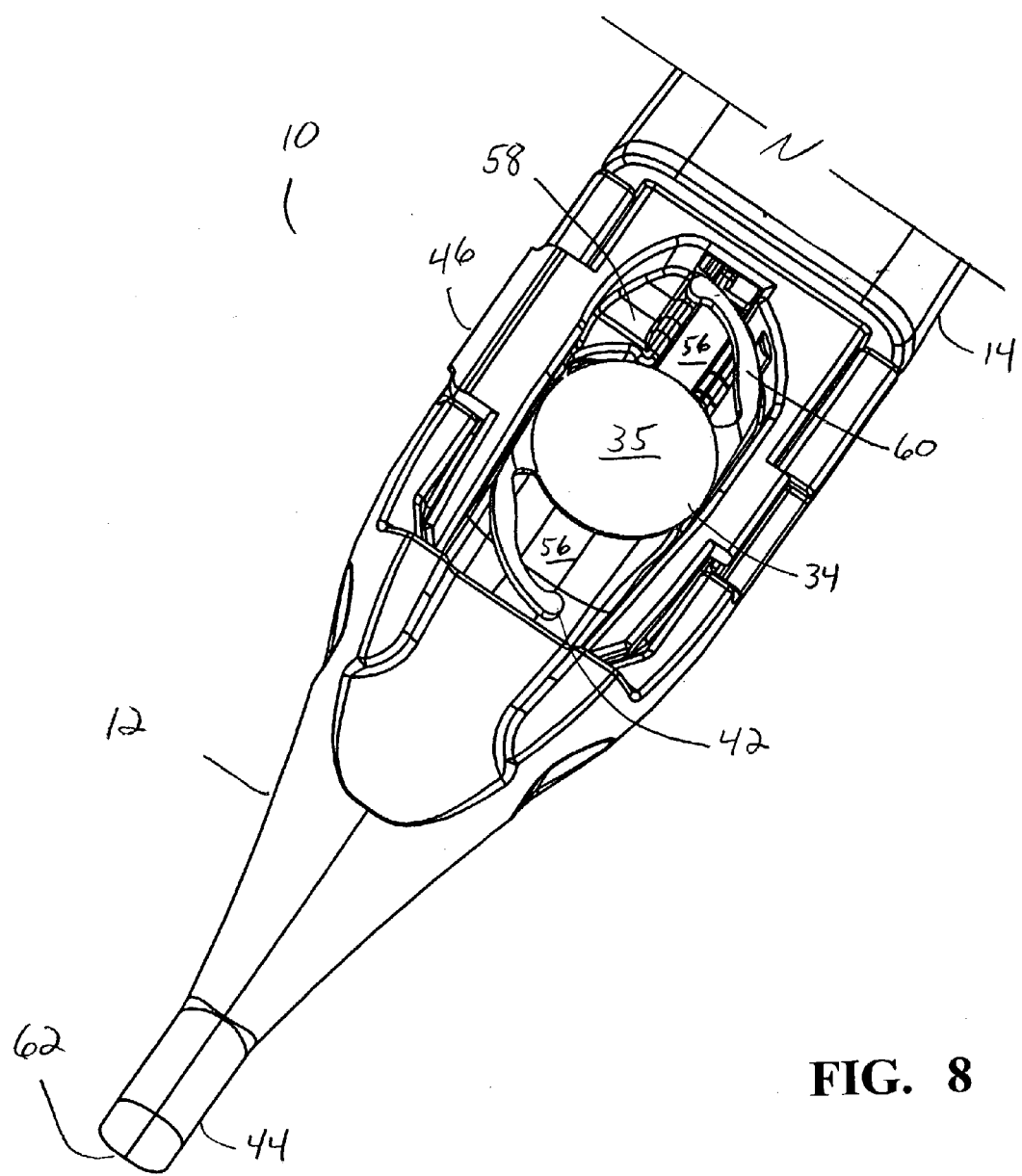
FIG. 8 is an exploded perspective view of the cartridge used with the lens delivery system of the present invention, showing the cartridge with the lens stop removed and the hinged lid removed.
Figure 9:
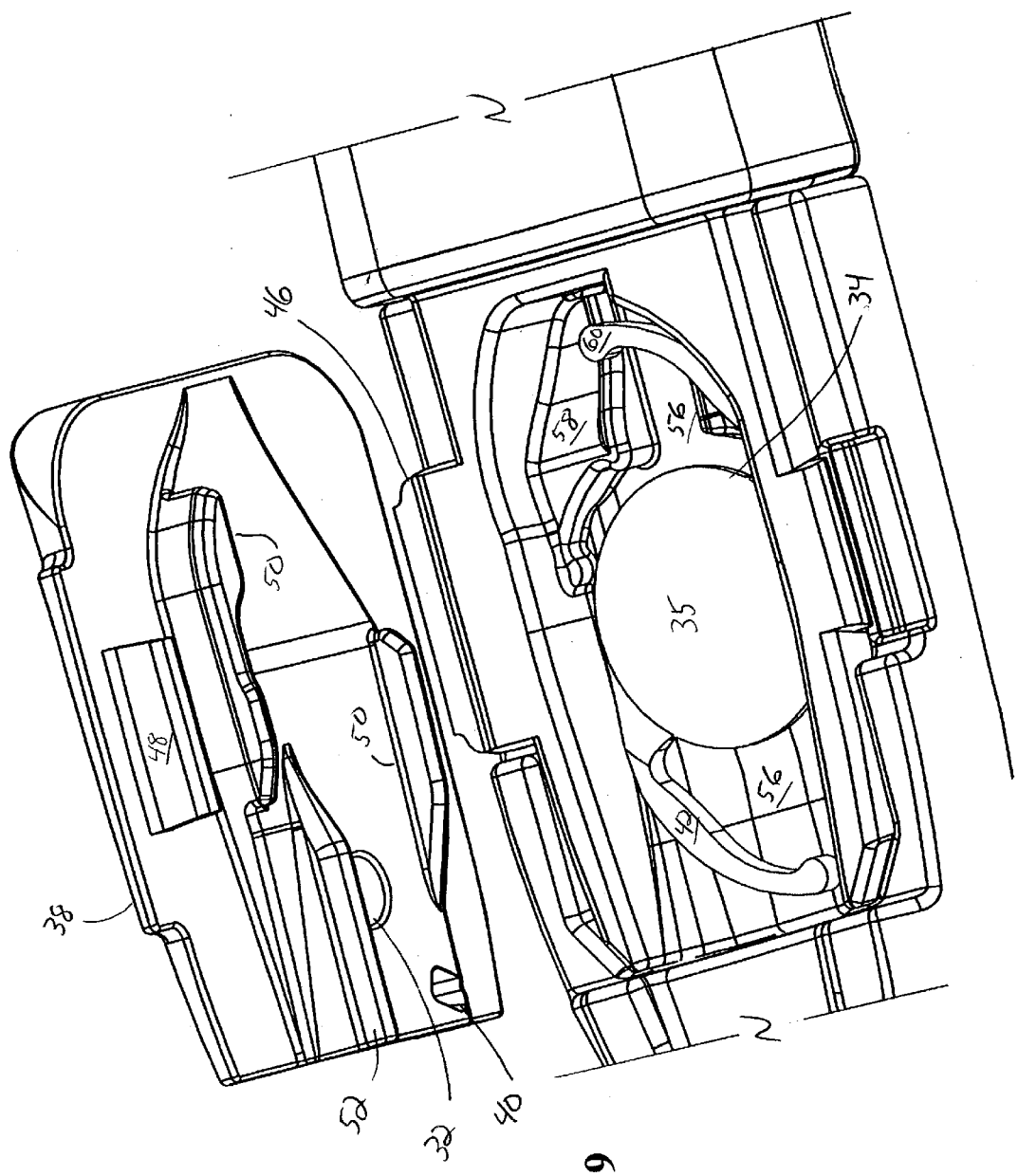
FIG. 9 is an exploded perspective view of the lens holding platform portion of the cartridge used with the lens delivery system of the present invention, showing the cartridge with the lens stop removed and the hinged lid open to expose the lens.

Nozzle portion 12 preferably is hollow on the inside and contains distal nozzle tube 44 of a size suitable for folding lens 34 to a suitably small size, e.g. 1.5 millimeters to 3.5 millimeters in diameter. Lid 38 is mounted to nozzle portion 12 by hinge 46 and contains clasp 48 to hold lid 38 in a closed position on nozzle portion 12. Lid also contains ribs 50 and 52. Ribs 50 hold the edges of optic 35 of IOL 34 to help prevent IOL 34 from moving within nozzle portion 12 during shipment. Rib 52 assists in the folding of IOL 34 by preventing IOL 34 from bending upward as IOL 34 is pushed down nozzle tube. As best seen in FIG. 5, sloped portion 54 of floor 56 also assists in the folding of IOL 34 by causing the edges of IOL 34 upward while the central portion of IOL 34 is prevented from moving upward by rib 52. Floor 56 of nozzle portion 12 contains a ramped portion 58 at the base of which trailing haptic 60 rests.

In use, a viscoelastic material is injected through channeled port 36 and port 40 into nozzle portion 12 so as to flex leading haptic 42 proximally against IOL 34. Stop 26 is removed from lid 38 of nozzle portion 12. Plunger 16 is pushed forward, contacting trailing haptic 60 on IOL 34 and pushing trailing haptic 60 up ramp 58, bending haptic 60 up and over IOL 34. Further forward movement of plunger 16 forces IOL 34 past ribs 50 and into nozzle tube. Sloped portion 54 on floor 56 causes the side edges of IOL 34 to bend upward while rib 52 restrains the central portion of IOL 34 from bending. Further distal movement of IOL 34 by plunger 16 causes further folding of IOL 34 and eventual expression of IOL 34 out distal end 62 of nozzle tube.

While certain embodiments of the present invention have been described above, these descriptions are given for purposes of illustration and explanation. Variations, changes, modifications and departures from the systems and methods disclosed above may be adopted without departure from the scope or spirit of the present invention.

We claim:

1. An intraocular lens delivery system, comprising:
   a) a injector body;
   b) a plunger adapted to reciprocate within the injector body;
   c) a nozzle portion having a hollow interior received on the distal end of the injector body, the nozzle portion having a removable lid;
   d) a nozzle tube on the distal end of the nozzle portion; and
   e) a stop frictionally engaged on the lid, the stop having a pin that projects into the hollow interior, the stop preventing movement of an intraocular lens contained within the hollow interior of the nozzle portion.

2. The lens delivery system of claim 1 wherein the stop helps prevent movement of an intraocular lens contained within the hollow body of the nozzle portion.

3. The lens delivery system of claim 1 wherein the lid further comprises a plurality of ribs suitable for holding an intraocular lens contained within the nozzle portion.

4. The lens delivery system of claim 1 wherein the stop further comprises a channeled port in fluid communication with the hollow interior of the nozzle portion.

5. The lens delivery system of claim 1 wherein the lid is hingedly connected to the nozzle portion.

6. The lens delivery system of claim 1 wherein the hollow interior of the nozzle portion has a rounded floor with a ramp, the rounded shape of the floor and the ramp assisting in the folding of an intraocular lens as the intraocular lens is pushed down the nozzle tube by the plunger.

7. The lens delivery system of claim 1 wherein the plunger further comprises a distal tip having a biasing tab.

8. An intraocular lens delivery system, comprising:
   a) a injector body;
   b) a plunger adapted to reciprocate within the injector body, the plunger having a distal tip with a biasing tab;
   c) a nozzle portion having a hollow interior received on the distal end of the injector body, the nozzle portion having a removable lid with a plurality of ribs suitable for holding an intraocular lens contained within the nozzle portion;
   d) a nozzle tube on the distal end of the nozzle portion; and
   e) a stop frictionally engaged on the lid, the stop having a pin that projects into the hollow interior, the stop preventing movement of an intraocular lens contained within the hollow interior of the nozzle portion.

9. The lens delivery system of claim 8 wherein the stop helps prevent movement of an intraocular lens contained within the hollow body of the nozzle portion.

10. The lens delivery system of claim 9 wherein the stop further comprises a channeled port in fluid communication with the hollow interior of the nozzle portion.

11. The lens delivery system of claim 8 wherein the lid is hingedly connected to the nozzle portion.

12. The lens delivery system of claim 8 wherein the hollow interior of the nozzle portion has a rounded floor with a ramp, the rounded shape of the floor and the ramp assisting in the folding of an intraocular lens as the intraocular lens is pushed down the nozzle tube by the plunger.

13. An intraocular lens delivery system, comprising:
a) a injector body;
b) a plunger adapted to reciprocate within the injector body;
c) a nozzle portion having a hollow interior received on the distal end of the injector body, the nozzle portion having a removable lid;
d) a nozzle tube on the distal end of the nozzle portion;
e) a hole in the lid, the hole communicating with the hollow interior of the nozzle portion; and
f) a stop having a pin that fits into the hole in the lid, the stop preventing movement of an intraocular lens contained within the hollow interior of the nozzle portion.

14. The lens delivery system of claim 13 wherein the lid further comprises a plurality of ribs suitable for holding an intraocular lens contained within the nozzle portion.

15. The lens delivery system of claim 13 wherein the stop further comprises a channeled port in fluid communication with the hole in the lid.

16. The lens delivery system of claim 13 wherein the lid is hingedly connected to the nozzle portion.

17. The lens delivery system of claim 13 wherein the hollow interior of the nozzle portion has a rounded floor with a ramp, the rounded shape of the floor and the ramp assisting in the folding of an intraocular lens as the intraocular lens is pushed down the nozzle tube by the plunger.

18. The lens delivery system of claim 13 wherein the plunger further comprises a distal tip having a biasing tab.

* * * * *